(12) United States Patent
Rubie et al.

(10) Patent No.: US 8,771,372 B1
(45) Date of Patent: Jul. 8, 2014

(54) LOWER LIMB PROSTHETIC DEVICE WITH A WAVE SPRING

(75) Inventors: Eric W. Rubie, Salt Lake City, UT (US); John S. Stites, Salt Lake City, UT (US)

(73) Assignee: Stealth Composites, LLC, Salt Lake City, UT (US)

( * ) Notice: Subject to any disclaimer, the term of this patent is extended or adjusted under 35 U.S.C. 154(b) by 0 days.

(21) Appl. No.: 13/200,689

(22) Filed: Sep. 28, 2011

Related U.S. Application Data

(60) Provisional application No. 61/404,154, filed on Sep. 28, 2010.

(51) Int. Cl.
*A61F 2/66* (2006.01)
*A61F 2/50* (2006.01)

(52) U.S. Cl.
CPC ............. *A61F 2/66* (2013.01); *A61F 2/6607* (2013.01); *A61F 2002/5007* (2013.01); *A61F 2002/6657* (2013.01); *A61F 2002/6664* (2013.01); *A61F 2002/6671* (2013.01); *A61F 2002/6678* (2013.01)
USPC .............................................. 623/55; 623/52

(58) Field of Classification Search
USPC ................. 623/47, 48, 49, 50, 52, 53, 54, 55
See application file for complete search history.

(56) References Cited

U.S. PATENT DOCUMENTS

| | | | | |
|---|---|---|---|---|
| 4,721,510 A | * | 1/1988 | Cooper et al. | 623/55 |
| 5,507,838 A | * | 4/1996 | Chen | 623/55 |
| 5,944,760 A | * | 8/1999 | Christensen | 623/55 |
| 8,317,877 B2 | * | 11/2012 | Doddroe et al. | 623/55 |
| 2009/0265019 A1 | * | 10/2009 | Chritstensen | 623/55 |

* cited by examiner

*Primary Examiner* — Marcia Hoffman
(74) *Attorney, Agent, or Firm* — Chambliss, Bahner & Stophel, P.C.

(57) ABSTRACT

A prosthetic device including an upper member having an upper end and a lower end, a wave member having a toe end and a heel end, and a third member having a proximal end and a distal end. In the preferred prosthetic device, the toe end of the wave member is fixedly attached to the upper member and the heel end of wave member is adapted to be deflected.

13 Claims, 12 Drawing Sheets

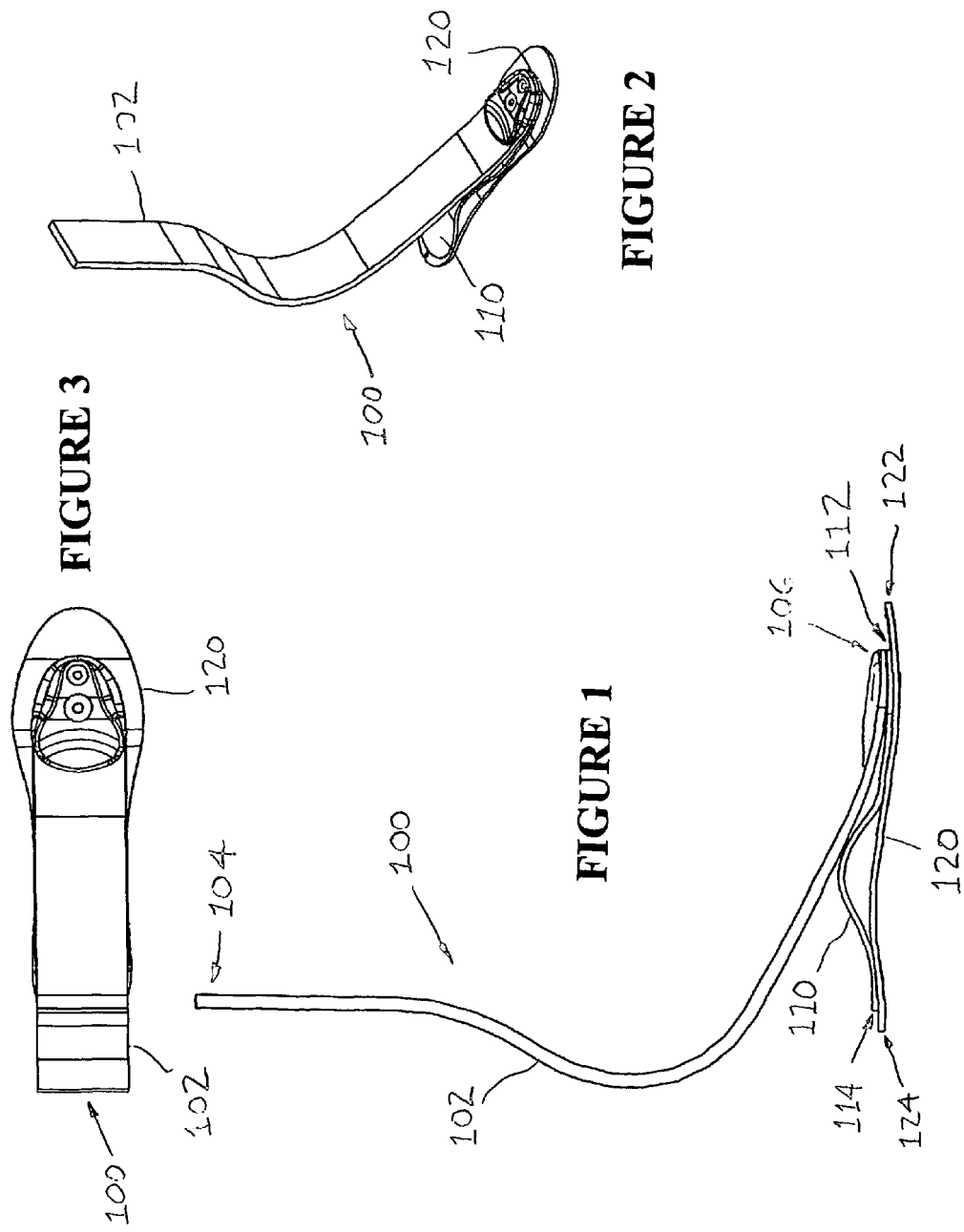

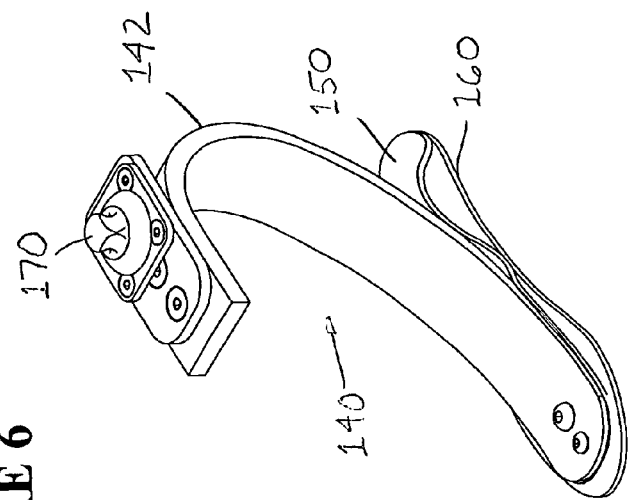
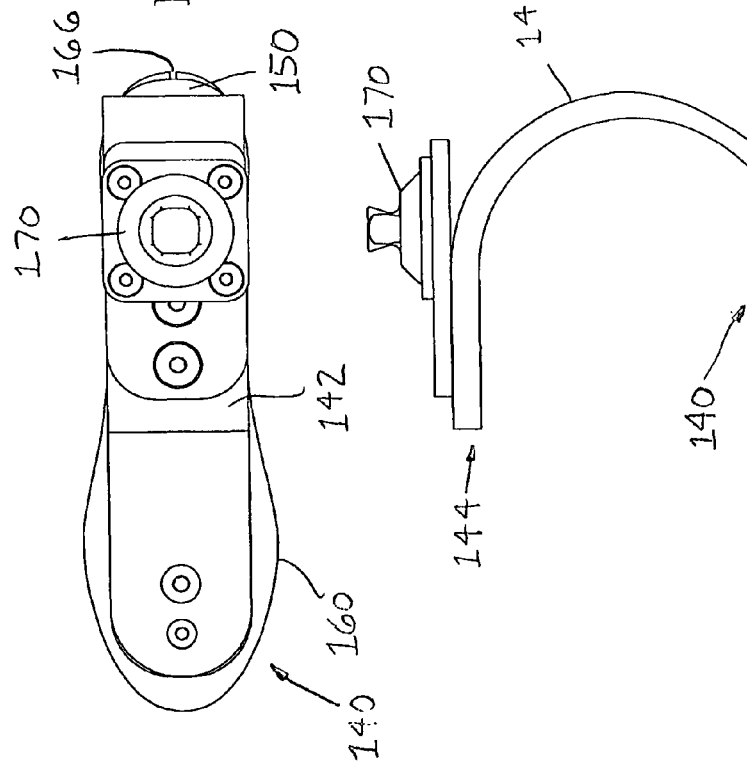

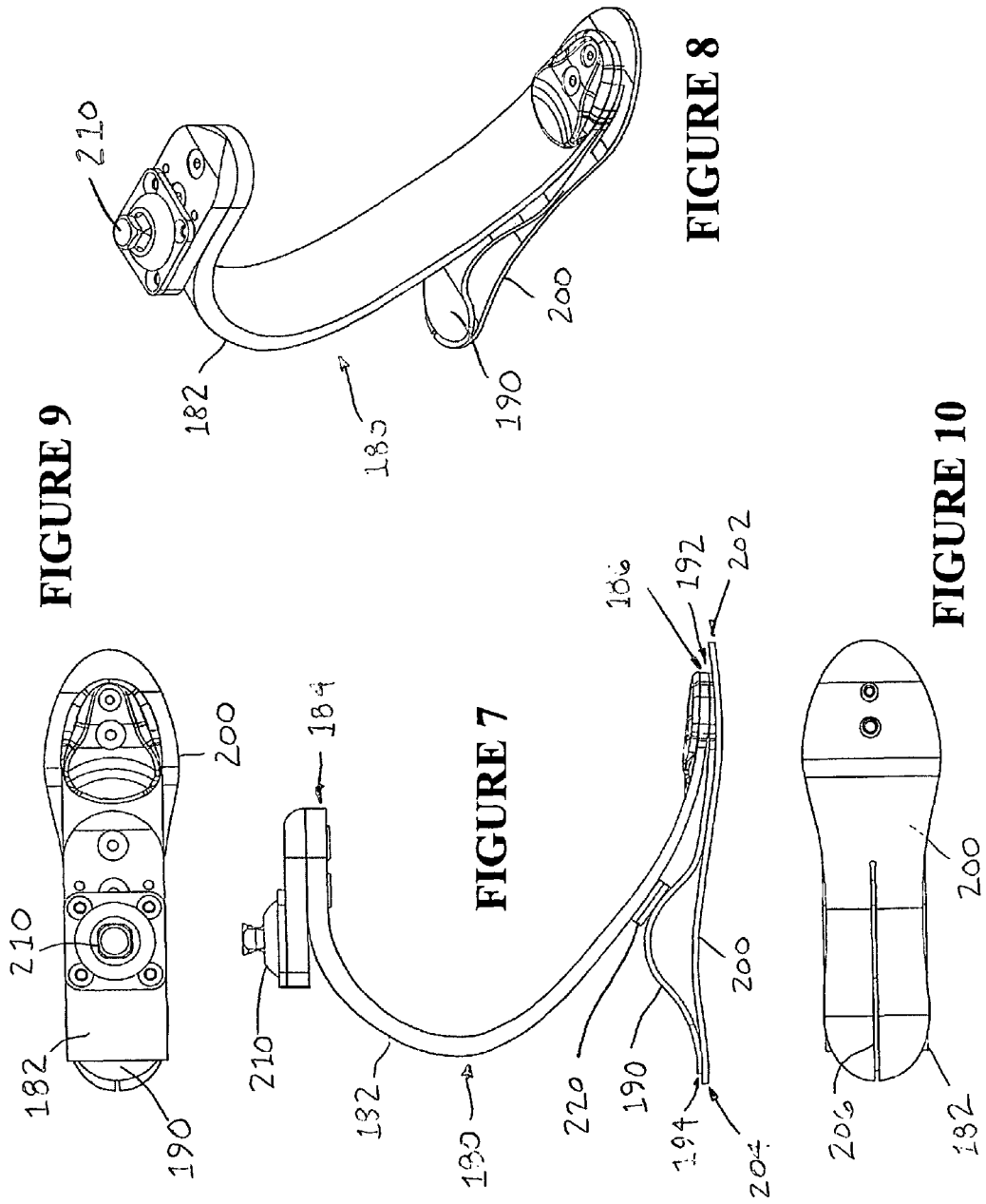

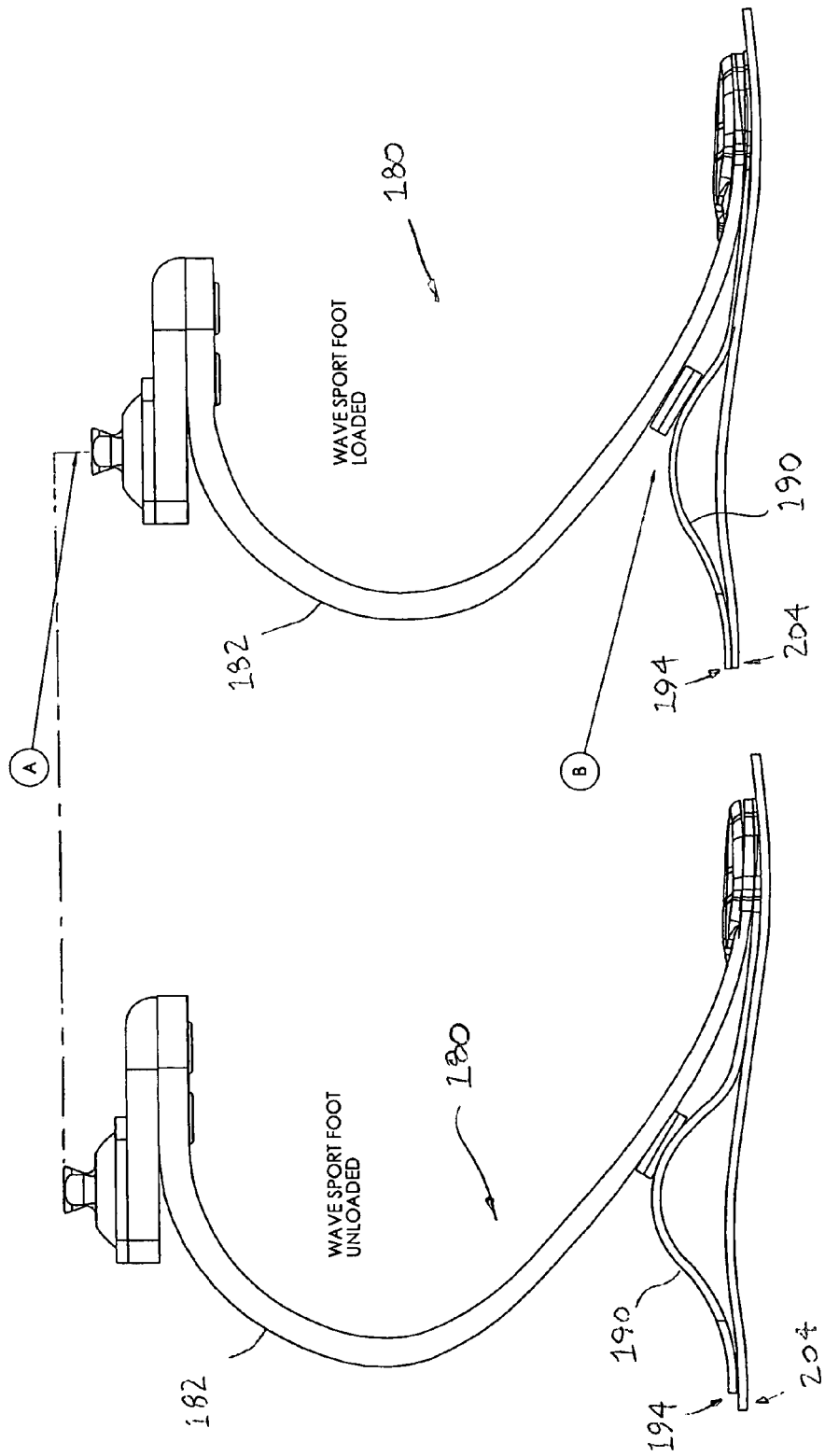

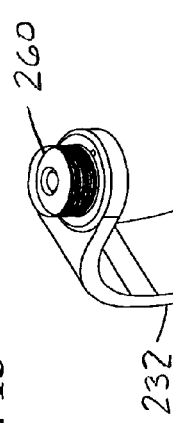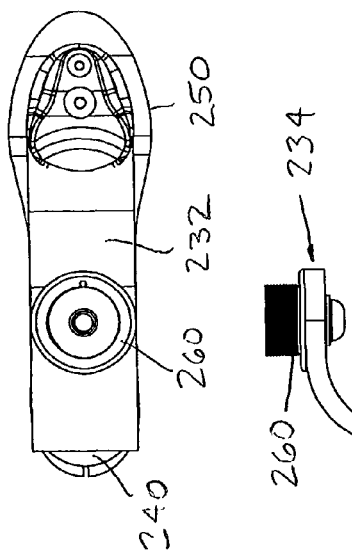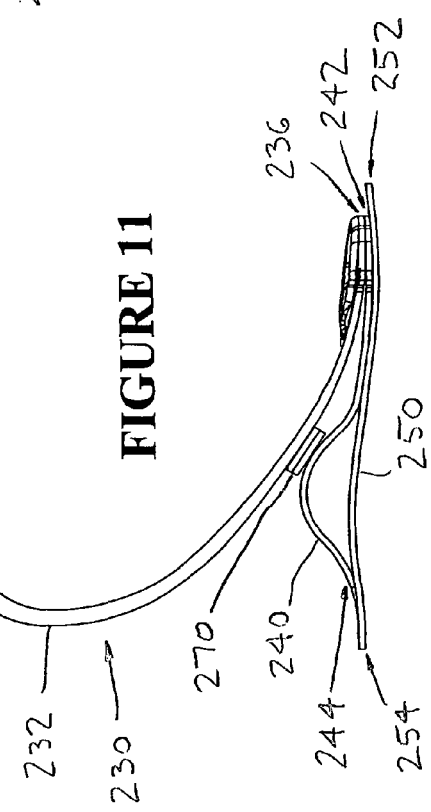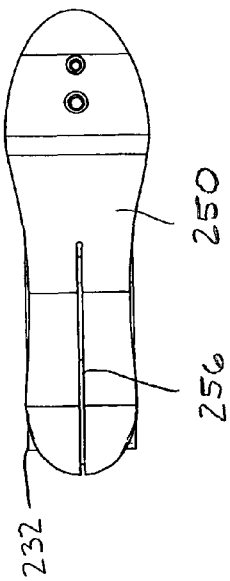

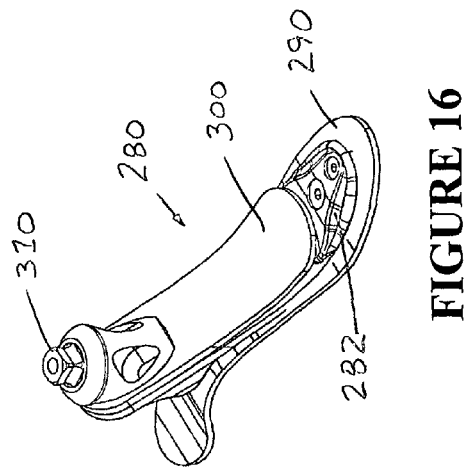
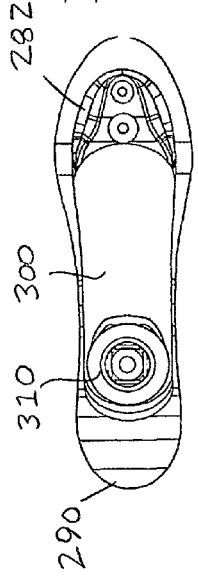
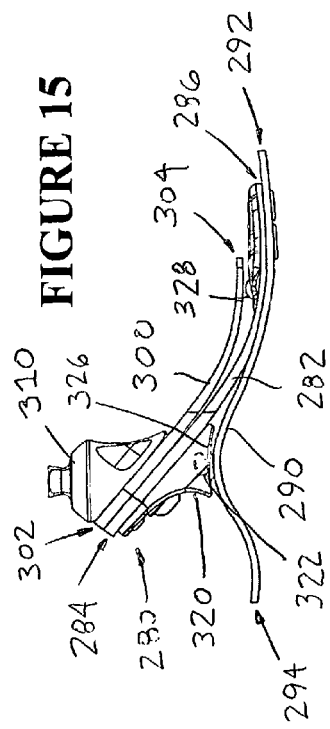
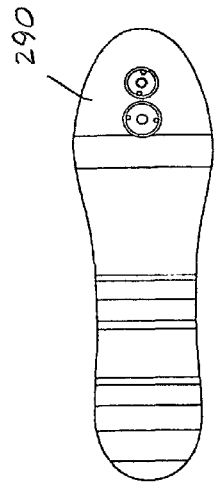

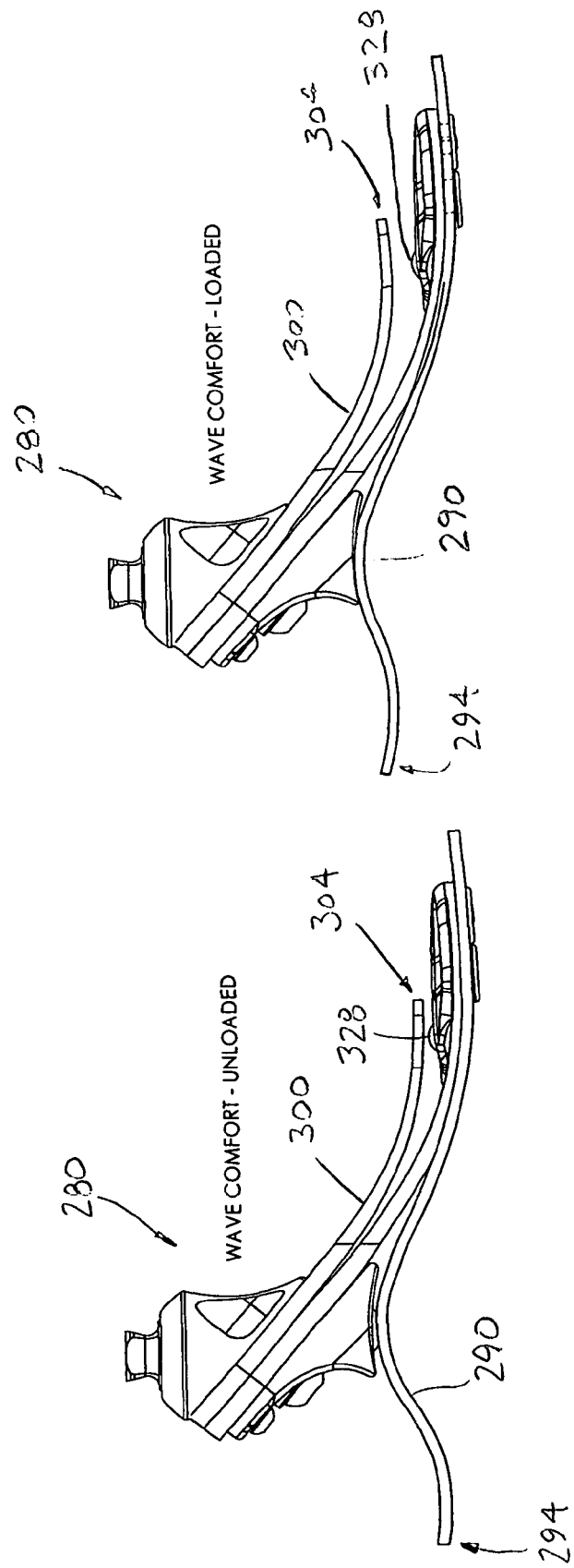

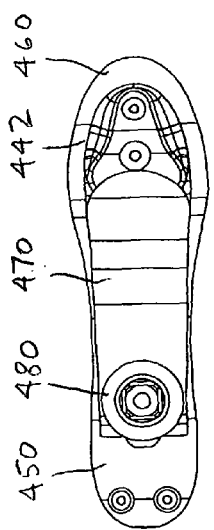
FIGURE 28
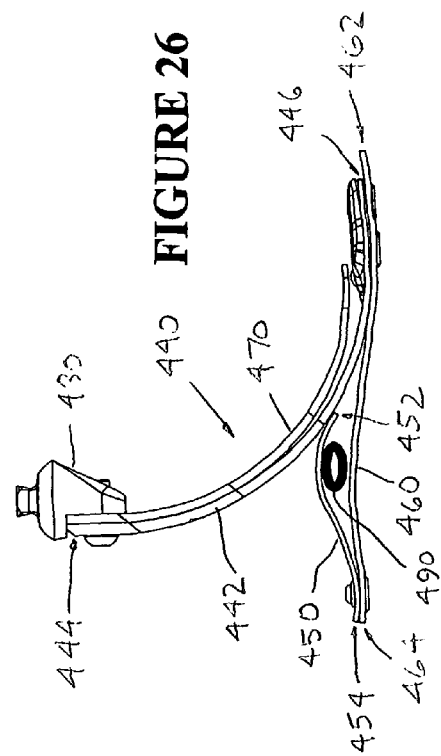
FIGURE 26
FIGURE 27
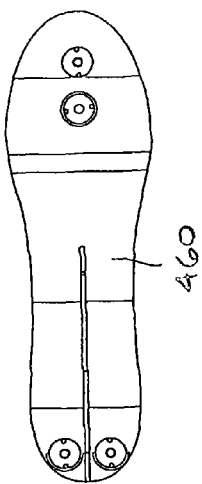
FIGURE 29

LOWER LIMB PROSTHETIC DEVICE WITH A WAVE SPRING

CROSS-REFERENCES TO RELATED APPLICATIONS/PATENTS

This application relates back to and claims the benefit of priority from U.S. Provisional Patent Application No. 61/404,154 entitled "Foot Prosthetic with Wave Spring" and filed on Sep. 28, 2010.

FIELD OF THE INVENTION

The present invention relates generally to prosthetic devices, and particularly to prosthetic devices for the user's lower limbs.

BACKGROUND AND DESCRIPTION OF THE PRIOR ART

It is known to use a prosthetic device on a user's lower limb. Conventional lower limb prosthetic devices, however, suffer from one or more shortcomings. For example, conventional lower limb prosthetic devices do not sufficiently deflect and dampen the impact at heel strike. Conventional lower limb prosthetic devices are also undesirably heavy and large. In addition, conventional lower limb prosthetic devices also have undesirable vertical compliance and roll over characteristics. Conventional prosthetic devices are also undesirably complex and noisy and lack durability.

It would be desirable, therefore, if a lower limb prosthetic device could be provided that would sufficiently deflect and dampen the impact at heel strike. It would also be desirable if such an apparatus could be provided that would reduce the weight and size of the lower limb prosthetic device. It would be further desirable if such an apparatus could be provided that would improve vertical compliance and roll over characteristics of the prosthetic device.

Advantages of the Preferred Embodiments of the Invention

Accordingly, it is an advantage of the preferred embodiments of the invention claimed herein to provide a lower limb prosthetic device that increases the deflection and dampens the impact at heel strike. It is also an advantage of the preferred embodiments of the invention claimed herein to provide a lower limb prosthetic device that reduces the weight and size of the prosthetic device. It is a further advantage of the preferred embodiments of the invention claimed herein to provide a lower limb prosthetic device that improves the vertical compliance and roll over characteristics of the prosthetic device.

Additional advantages of the invention will become apparent from an examination of the drawings and the ensuing description.

SUMMARY OF THE INVENTION

The invention comprises a prosthetic device including an upper member having an upper end and a lower end, a wave member having a toe end and a heel end, and a third member having a proximal end and a distal end. In the preferred prosthetic device, the toe end of the wave member is fixedly attached to the upper member and the heel end of wave member is adapted to be deflected.

BRIEF DESCRIPTION OF THE DRAWINGS

The presently preferred embodiments of the invention are illustrated in the accompanying drawings, in which like reference numerals represent like parts throughout, and in which:

FIG. 1 is a front view of the preferred embodiment of the lower limb prosthetic device with a wave spring in accordance with the invention.

FIG. 2 is a perspective view of the preferred lower limb prosthetic device with a wave spring illustrated in FIG. 1.

FIG. 3 is a top view of the preferred lower limb prosthetic device illustrated in FIGS. 1-2.

FIG. 4 is a front view of a first alternative embodiment of the lower limb prosthetic device in accordance with the present invention.

FIG. 5 is a perspective view of the preferred lower limb prosthetic device illustrated in FIG. 4.

FIG. 6 is a top view of the preferred lower limb prosthetic device illustrated in FIGS. 4-5.

FIG. 7 is a second alternative embodiment of the lower limb prosthetic device in accordance with the present invention.

FIG. 7A is a front view of the preferred lower limb prosthetic device illustrated in FIG. 7 showing the device in an unloaded condition.

FIG. 7B is a front view of the preferred lower limb prosthetic device illustrated in FIGS. 7 and 7A showing the device in a loaded condition.

FIG. 8 is a perspective view of the preferred lower limb prosthetic device illustrated in FIG. 7.

FIG. 9 is a top view of the preferred lower limb prosthetic device illustrated in FIGS. 7-8.

FIG. 10 is a bottom view of the preferred lower limb prosthetic device illustrated in FIGS. 7-9.

FIG. 11 is a front view of a third alternative embodiment of the lower limb prosthetic device in accordance with the present invention.

FIG. 12 is a perspective view of the preferred lower limb prosthetic device illustrated in FIG. 11.

FIG. 13 is a top view of the preferred lower limb prosthetic device illustrated in FIGS. 11-12.

FIG. 14 is a bottom view of the preferred lower limb prosthetic device illustrated in FIGS. 11-13.

FIG. 15 is a front view of a fourth alternative embodiment of the lower limb prosthetic device in accordance with the present invention.

FIG. 15A is a front view of the preferred lower limb prosthetic device illustrated in FIG. 15 in an unloaded condition.

FIG. 15B is a front view of the preferred lower limb prosthetic device illustrated in FIGS. 15-15A in a loaded condition.

FIG. 16 is a perspective view of the preferred lower limb prosthetic device illustrated in FIGS. 15-15C.

FIG. 17 is a top view of the preferred lower limb prosthetic device illustrated in FIGS. 15-16.

FIG. 18 is a bottom view of the preferred lower limb prosthetic device illustrated in FIGS. 15-17.

FIG. 26 is a front view of a seventh alternative embodiment of the lower limb prosthetic device in accordance with the present invention.

FIG. 27 is a perspective view of the preferred lower limb prosthetic device illustrated in FIG. 26.

FIG. 28 is a top view of the preferred lower limb prosthetic device illustrated in FIGS. 26-27.

FIG. 29 is a bottom view of the preferred lower limb prosthetic device illustrated in FIG. 26-28.

DESCRIPTION OF THE PREFERRED EMBODIMENTS OF THE INVENTION

Figure 15C:
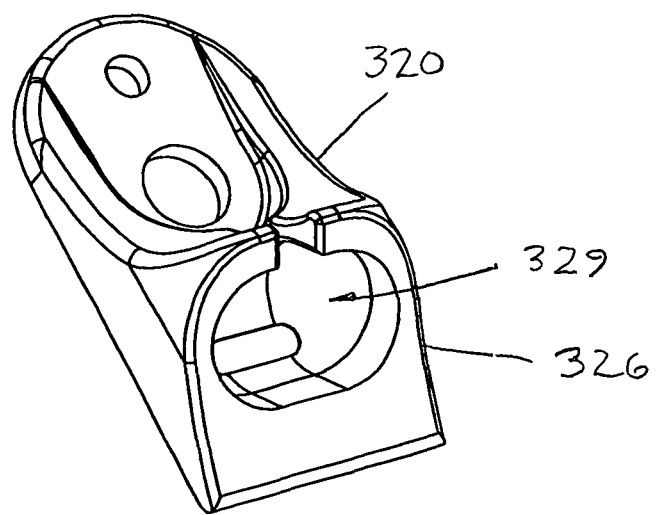
FIG. 15C is a perspective view of the preferred progressive stop illustrated in FIGS. 15-15B.

Referring now to the drawings, the preferred embodiments of the lower limb prosthetic device with a wave spring are illustrated by FIGS. 1 through 32. As shown in FIGS. 1-32, the preferred lower limb prosthetic devices are adapted to increase the deflection and dampen the impact at heel strike. The preferred lower limb prosthetic devices are also adapted to reduce the weight and size of the prosthetic device. The preferred lower limb prosthetic devices are further adapted to improve the vertical compliance and roll over characteristics of the prosthetic device.

Referring now to FIG. 1, a front view of the preferred embodiment of the lower limb prosthetic device with a wave spring is illustrated. As shown in FIG. 1, the preferred lower limb prosthetic device is designated generally by reference numeral 100. The preferred lower limb prosthetic device 100 is adapted to be worn on a user's lower limb. The preferred lower limb prosthetic device 100 comprises upper member 102 which has upper end 104 and lower end 106. The preferred lower limb prosthetic device 100 also comprises wave member 110 which has toe end 112 and heel end 114. The preferred lower limb prosthetic device 100 further comprises third member 120 which has proximal end 122 and distal end 124. In the preferred lower limb prosthetic device 100, toe end 112 of wave member 110 is fixedly attached to upper member 102 and heel end 114 of the wave member is adapted to be deflected.

Still referring to FIG. 1, in the preferred lower limb prosthetic device 100, upper member 102 and wave member 110 are fixedly attached adjacent to lower end 106 of the upper member and toe end 112 of the wave member. Also in the preferred lower limb prosthetic device 100, proximal end 122 of third member 120 is fixedly attached adjacent to toe end 112 of wave member 110. The preferred wave member 110 comprises an arch and is resilient. In addition, preferred wave member 110 has an original configuration and is adapted to be compressed and elongated when a load is applied to the lower limb prosthetic device and return to the original configurations when the load is removed from the device. Further, the preferred lower limb prosthetic device 100 is adapted to provide transalatory movement and preferred wave member 110 is adapted to deflect along a horizontal plane and a vertical plane.

Referring now to FIG. 2, a perspective view of preferred lower limb prosthetic device 100 with a wave spring is illustrated. As shown in FIG. 2, preferred lower limb prosthetic device 100 comprises upper member 102, wave member 110 and third member 120.

Referring now to FIG. 3, a top view of the preferred lower limb prosthetic device 100 is illustrated. As shown in FIG. 3, preferred lower limb prosthetic device 100 comprises upper member 102 and third member 120. While FIGS. 1-3 illustrate the preferred configuration and arrangement of lower limb prosthetic device 100, it is contemplated within the scope of the invention that the lower limb prosthetic device may be of any suitable configuration and arrangement.

Referring now to FIG. 4, a front view of a first alternative embodiment of the lower limb prosthetic device is illustrated. As shown in FIG. 4, the preferred lower limb prosthetic device is designated generally by reference numeral 140. The preferred lower limb prosthetic device 140 comprises upper member 142 which has upper end 144 and lower end 146. The preferred lower limb prosthetic device 140 also comprises wave member 150 which has toe end 152 and heel end 154. The preferred lower limb prosthetic device 140 further comprises third member 160 which has proximal end 162 and distal end 164. In the preferred lower limb prosthetic device 140, toe end 152 of wave member 150 is fixedly attached to upper member 142 and heel end 154 of the wave member is adapted to be deflected. The preferred lower limb prosthetic device 140 still further comprises mounting device 170.

Referring now to FIG. 5, a perspective view of the preferred lower limb prosthetic device 140 is illustrated. As shown in FIG. 5, preferred lower limb prosthetic device 140 comprises upper member 142, wave member 150, third member 160 and mounting device 170.

Referring now to FIG. 6, a top view of the preferred lower limb prosthetic device 140 is illustrated. As shown in FIG. 6, preferred lower limb prosthetic device 140 comprises upper member 142, wave member 150, third member 160, slot 166, and mounting device 170. While FIGS. 4-6 illustrate the preferred configuration and arrangement of lower limb prosthetic device 140, it is contemplated within the scope of the invention that the lower limb prosthetic device may be of any suitable configuration and arrangement.

Referring now to FIG. 7, a second alternative embodiment of the lower limb prosthetic device is illustrated. As shown in FIG. 7, the preferred lower limb prosthetic device is designated generally by reference numeral 180. The preferred lower limb prosthetic device 180 comprises upper member 182 which has upper end 184 and lower end 186. The preferred lower limb prosthetic device 180 also comprises wave member 190 which has toe end 192 and heel end 194. The preferred lower limb prosthetic device 180 further comprises third member 200 which has proximal end 202 and distal end 204. In the preferred lower limb prosthetic device 180, toe end 192 of wave member 190 is fixedly attached to upper member 182 and heel end 194 of the wave member is adapted to be deflected. The preferred lower limb prosthetic device 180 still further comprises mounting device 210 and dampener 220. The preferred elastomeric dampener 220 is elastomeric and resilient and adapted to reduce noise produced by the device.

Referring now to FIG. 7A, a front view of preferred lower limb prosthetic device 180 in an unloaded condition. As shown in FIG. 7A, the heel end 194 of wave member 190 does not extend to the distal end 204 of third member 200.

Referring now to FIG. 7B, a front view of preferred lower limb prosthetic device 180 in a loaded condition. As shown in FIG. 7B, heel end 194 of wave member 190 extends slightly beyond distal end 204 of third member 200 when a downward force is applied to upper member 182. As shown by reference letters A and B, preferred mounting device 210 and wave member 190 are vertically displaced in a downward direction when a downward force is applied to upper member 182.

Referring now to FIG. 8, a perspective view of the preferred lower limb prosthetic device 180 is illustrated. As shown in FIG. 8, preferred lower limb prosthetic device 180 comprises upper member 182, wave member 190, third member 200 and mounting device 210.

Referring now to FIG. 9, a top view of the preferred lower limb prosthetic device 180 is illustrated. As shown in FIG. 9, preferred lower limb prosthetic device 180 comprises upper member 182, wave member 190, third member 200 and mounting device 210.

Referring now to FIG. 10, a bottom view of the preferred lower limb prosthetic device 180 is illustrated. As shown in FIG. 10, preferred lower limb prosthetic device 180 comprises upper member 182, third member 200 and slot 206. While FIGS. 7-10 illustrate the preferred configuration and arrangement of lower limb prosthetic device 180, it is contemplated within the scope of the invention that the lower limb prosthetic device may be of any suitable configuration and arrangement.

Referring now to FIG. 11, a front view of a third alternative embodiment of the lower limb prosthetic device is illustrated. As shown in FIG. 11, the preferred lower limb prosthetic device is designated generally by reference numeral 230. The preferred lower limb prosthetic device 230 comprises upper member 232 which has upper end 234 and lower end 236. The preferred lower limb prosthetic device 230 also comprises wave member 240 which has toe end 242 and heel end 244. The preferred lower limb prosthetic device 230 further comprises third member 250 which has proximal end 252 and distal end 254. In the preferred lower limb prosthetic device 230, toe end 242 of wave member 240 is fixedly attached to upper member 232 and heel end 244 of the wave member is adapted to be deflected. The preferred lower limb prosthetic device 230 still further comprises mounting device 260 and dampener 270.

Referring now to FIG. 12, a perspective view of the preferred lower limb prosthetic device 230 is illustrated. As shown in FIG. 12, preferred lower limb prosthetic device 230 comprises upper member 232, wave member 240, third member 250 and mounting device 260.

Referring now to FIG. 13, a top view of the preferred lower limb prosthetic device 230 is illustrated. As shown in FIG. 13, preferred lower limb prosthetic device 230 comprises upper member 232, wave member 240, third member 250 and mounting device 260.

Referring now to FIG. 14, a bottom view of the preferred lower limb prosthetic device 230 is illustrated. As shown in FIG. 14, preferred lower limb prosthetic device 230 comprises upper member 232, third member 250 and slot 256. While FIGS. 11-14 illustrate the preferred configuration and arrangement of lower limb prosthetic device 230, it is contemplated within the scope of the invention that the lower limb prosthetic device may be of any suitable configuration and arrangement.

Referring now to FIG. 15, a front view of a fourth alternative embodiment of the lower limb prosthetic device is illustrated. As shown in FIG. 15, the preferred lower limb prosthetic device is designated generally by reference numeral 280. The preferred lower limb prosthetic device 280 comprises upper member 282 which has upper end 284 and lower end 286. The preferred lower limb prosthetic device 280 also comprises wave member 290 which has toe end 292 and heel end 294. The preferred lower limb prosthetic device 280 further comprises third member 300 which has proximal end 302 and distal end 304. In the preferred lower limb prosthetic device 280, toe end 292 of wave member 290 is fixedly attached to upper member 282 and heel end 294 of the wave member is adapted to be deflected. Also in the preferred lower limb prosthetic device 280, proximal end 302 of third member 300 is fixedly attached adjacent to upper end 284 of upper member 282. The preferred lower limb prosthetic device 280 still further comprises mounting device 310, progressive stop 320 and heel dampener 322. The preferred progressive stop 320 includes recess 324 which is adapted to hold preferred dampener 322. The preferred progressive stop 320 also includes curved contact surface 326 which is adapted to transmit loads during walking as well as support the ultimate loads applied during certification testing. In addition, the preferred lower limb prosthetic device 280 includes toe dampener 328 which is adapted to be contacted by third member 300 adjacent to proximal end 302.

Still referring to FIG. 15, when a load is initially applied to heel end 294 of wave member 290 of preferred lower limb prosthetic device 280, heel dampener 322 absorbs the initial shock force at heel strike. Also at heel strike, distal end 304 of third member 300 begins to move upwardly away from lower end 286 of upper member 282. This action provides enhanced plantar flexion. During heel loading, progressive stop 320 produces a fulcrum that supports wave member 290 and absorbs the load to produce a smooth and uniform transmission of the forces for a fluid gait pattern. After the initial heel strike and until heel off, wave member 290 is deflected and extended to provide optimal shock absorption. As wave member 290 extends, distal end 304 of third member 300 contacts dampener 328 to provide a progressive dynamic response. As preferred lower limb prosthetic device 280 moves from forefoot to heel off, wave member 290 opens for a smooth, stable progression.

Referring now to FIG. 15A, a front view of preferred lower limb prosthetic device 280 in an unloaded condition. As shown in FIG. 15A, distal end 304 of third member 300 is disposed near toe dampener 328 when the device is in an unloaded condition.

Referring now to FIG. 15B, a front view of preferred lower limb prosthetic device 280 in a loaded condition. As shown in FIG. 15B, distal end 304 of third member 300 is displace upwardly and away from toe dampener 328 when heal end 294 of wave member 290 is displaced upwardly such as at heel strike.

Referring now to FIG. 15C, a perspective view of preferred progressive stop 320 is illustrated. As shown in FIG. 15C, preferred progressive stop 320 includes recess 329.

Referring now to FIG. 16, a perspective view of preferred lower limb prosthetic device 280 is illustrated. As shown in FIG. 16, preferred lower limb prosthetic device 280 comprises upper member 282, wave member 290, third member 300 and mounting device 310.

Referring now to FIG. 17, a top view of preferred lower limb prosthetic device 280 is illustrated. As shown in FIG. 17, preferred lower limb prosthetic device 280 comprises upper member 282, wave member 290, third member 300 and mounting device 310.

Referring now to FIG. 18, a bottom view of the preferred lower limb prosthetic device 280 is illustrated. As shown in FIG. 18, preferred lower limb prosthetic device 280 comprises wave member 290. While FIGS. 15-18 illustrate the preferred configuration and arrangement of lower limb prosthetic device 280, it is contemplated within the scope of the invention that the lower limb prosthetic device may be of any suitable configuration and arrangement.

Figure 19:
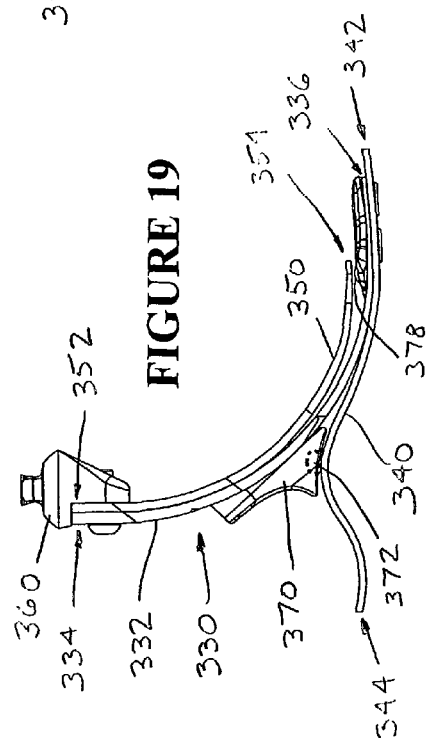
FIG. 19 is a front view of a fifth alternative embodiment of the lower limb prosthetic device in accordance with the present invention.

Referring now to FIG. 19, a front view of a fifth alternative embodiment of the lower limb prosthetic device is illustrated. As shown in FIG. 19, the preferred lower limb prosthetic device is designated generally by reference numeral 330. The preferred lower limb prosthetic device 330 comprises upper member 332 which has upper end 334 and lower end 336. The preferred lower limb prosthetic device 330 also comprises wave member 340 which has toe end 342 and heel end 344. The preferred lower limb prosthetic device 330 further comprises third member 350 which has proximal end 352 and distal end 354. In the preferred lower limb prosthetic device 330, toe end 342 of wave member 340 is fixedly attached to upper member 332 and heel end 344 of the wave member is adapted to be deflected. Also in the preferred lower limb prosthetic device 330, proximal end 352 of third member 350 is fixedly attached adjacent to upper end 334 of upper member 332. The preferred lower limb prosthetic device 330 still further comprises mounting device 360, progressive stop 370 and heel dampener 372. In addition, the preferred lower limb prosthetic device 330 includes toe dampener 378.

Figure 20:
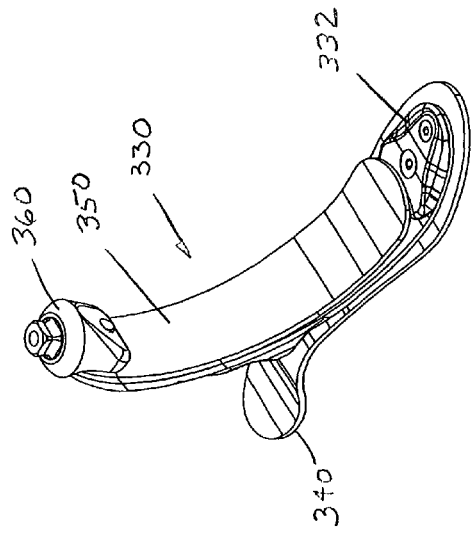
FIG. 20 is a perspective view of the preferred lower limb prosthetic device illustrated in FIG. 19.

Referring now to FIG. 20, a perspective view of the preferred lower limb prosthetic device 330 is illustrated. As shown in FIG. 20, preferred lower limb prosthetic device 330 comprises upper member 332, wave member 340, third member 350 and mounting device 360.

Figure 21:
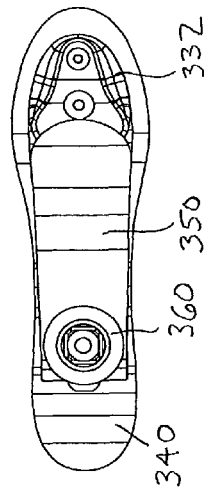
FIG. 21 is a top view of the preferred lower limb prosthetic device illustrated in FIGS. 19-20.

Referring now to FIG. 21, a top view of the preferred lower limb prosthetic device 330 is illustrated. As shown in FIG. 21, preferred lower limb prosthetic device 330 comprises upper member 332, wave member 340, third member 350 and mounting device 360.

Figure 22:
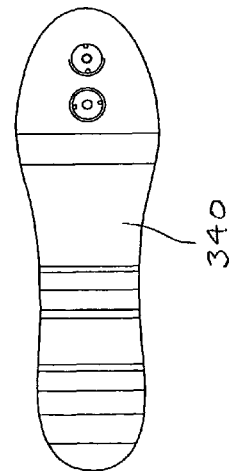
FIG. 22 is a bottom view of the preferred lower limb prosthetic device illustrated in FIGS. 19-21.

Referring now to FIG. 22, a bottom view of the preferred lower limb prosthetic device 330 is illustrated. As shown in FIG. 22, preferred lower limb prosthetic device 330 comprises wave member 340. While FIGS. 19-22 illustrate the preferred configuration and arrangement of lower limb prosthetic device 330, it is contemplated within the scope of the invention that the lower limb prosthetic device may be of any suitable configuration and arrangement.

Figure 23:
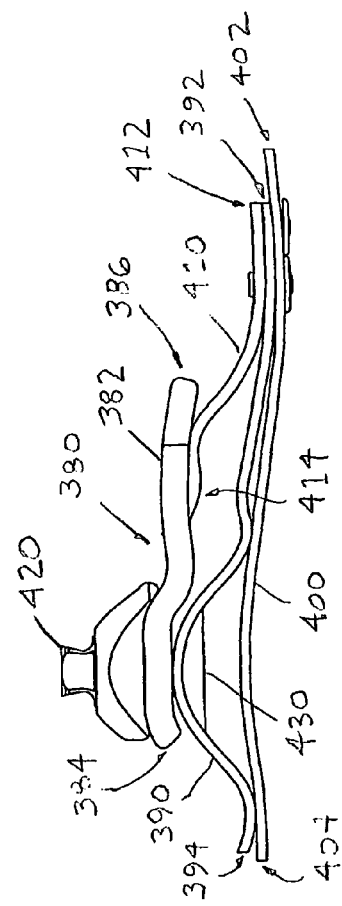
FIG. 23 is a front view of a sixth alternative embodiment of the lower limb prosthetic device in accordance with the present invention.

Referring now to FIG. 23, a front view of a sixth alternative embodiment of the lower limb prosthetic device is illustrated. As shown in FIG. 23, the preferred lower limb prosthetic device is designated generally by reference numeral 380. The preferred lower limb prosthetic device 380 comprises upper member 382 which has upper end 384 and lower end 386. The preferred lower limb prosthetic device 380 also comprises wave member 390 which has toe end 392 and heel end 394. The preferred lower limb prosthetic device 380 further comprises third member 400 which has proximal end 402 and distal end 404. The preferred lower limb prosthetic device 380 still further comprises fourth member 410 which is fixedly attached adjacent to toe end 392 of wave member 390 and is adapted to contact lower end 386 of upper member 382. The preferred fourth member 410 is a leaf spring having anterior end 412 and posterior end 414. In the preferred lower limb prosthetic device 380, toe end 392 of wave member 390 is fixedly attached to proximal end 402 of third member 400, and heel end 394 of the wave member is adapted to be deflected. The preferred lower limb prosthetic device 380 still further comprises mounting device 420 and anchor 430.

Figure 24:
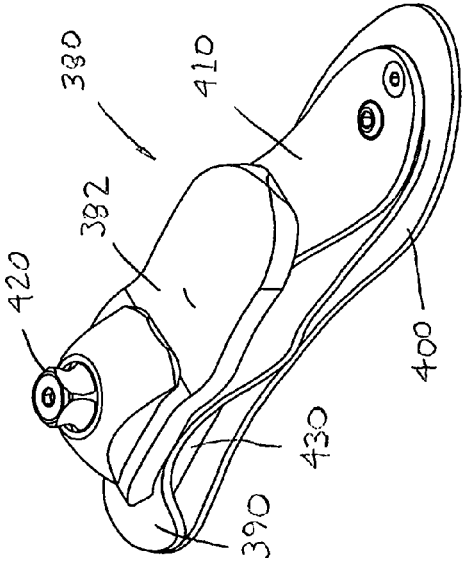
FIG. 24 is a perspective view of the preferred lower limb prosthetic device illustrated in FIG. 23.

Referring now to FIG. 24, a perspective view of the preferred lower limb prosthetic device 380 is illustrated. As shown in FIG. 24, preferred lower limb prosthetic device 380 comprises upper member 382, wave member 390, third member 400, fourth member 410 and mounting device 420.

Figure 25:
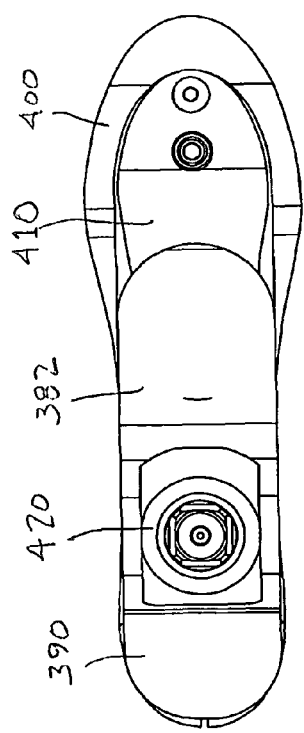
FIG. 25 is a top view of the preferred lower limb prosthetic device illustrated in FIGS. 23-24.

Referring now to FIG. 25, a top view of the preferred lower limb prosthetic device 380 is illustrated. As shown in FIG. 24, preferred lower limb prosthetic device 380 comprises upper member 382, wave member 390, third member 400, fourth member 410 and mounting device 420. While FIGS. 23-25 illustrate the preferred configuration and arrangement of lower limb prosthetic device 380, it is contemplated within the scope of the invention that the lower limb prosthetic device may be of any suitable configuration and arrangement.

Referring now to FIG. 26, a front view of a seventh alternative embodiment of the lower limb prosthetic device is illustrated. As shown in FIG. 26, the preferred lower limb prosthetic device is designated generally by reference numeral 440. The preferred lower limb prosthetic device 440 comprises upper member 442 which has upper end 444 and lower end 446. The preferred lower limb prosthetic device 440 also comprises wave member 450 which has toe end 452 and heel end 454. The preferred lower limb prosthetic device 440 further comprises third member 460 which has proximal end 462 and distal end 464. The preferred third member is fixedly attached to the lower end 446 of upper member 442. The preferred lower limb prosthetic device 440 still further comprises fourth member 470 which is fixedly attached adjacent to upper end 444 of upper member 442. In the preferred lower limb prosthetic device 440, heel end 454 of wave member 450 is fixedly attached adjacent to distal end 464 of third member 460, and toe end 452 of the wave member is adapted to be deflected. The preferred lower limb prosthetic device 440 still further comprises mounting device 480 and dampener 490.

Referring now to FIG. 27, a perspective view of the preferred lower limb prosthetic device 440 is illustrated. As shown in FIG. 27, preferred lower limb prosthetic device 440 comprises upper member 442, wave member 450, third member 460, fourth member 470 and mounting device 480.

Referring now to FIG. 28, a top view of the preferred lower limb prosthetic device 440 is illustrated. As shown in FIG. 28, preferred lower limb prosthetic device 440 comprises upper member 442, wave member 450, third member 460, fourth member 470 and mounting device 480.

Referring now to FIG. 29, a bottom view of the preferred lower limb prosthetic device 440 is illustrated. As shown in FIG. 29, preferred lower limb prosthetic device 440 comprises third member 460. While FIGS. 26-29 illustrate the preferred configuration and arrangement of lower limb prosthetic device 440, it is contemplated within the scope of the invention that the lower limb prosthetic device may be of any suitable configuration and arrangement.

Figure 30:
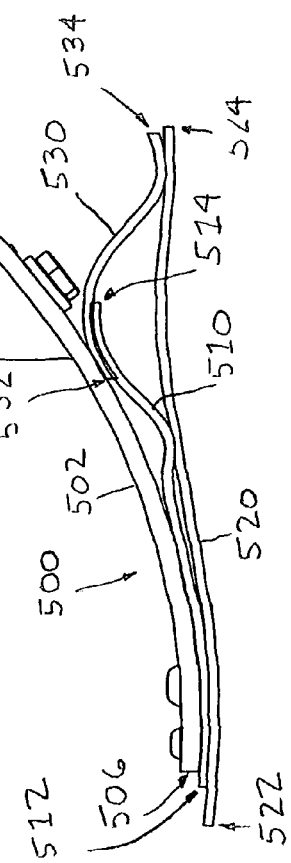
FIG. 30 is a front view of an eighth alternative embodiment of the lower limb prosthetic device in accordance with the present invention.

Referring now to FIG. 30, a front view of an eighth alternative embodiment of the lower limb prosthetic device is illustrated. As shown in FIG. 30, the preferred lower limb prosthetic device is designated generally by reference numeral 500. The preferred lower limb prosthetic device 500 comprises upper member 502 which has upper end 504 and lower end 506. The preferred lower limb prosthetic device 500 also comprises wave member 510 which has toe end 512 and heel end 514. The preferred lower limb prosthetic device 500 further comprises third member 520 which has proximal end 522 and distal end 524. In the preferred lower limb prosthetic device 500, toe end 512 of wave member 510 is fixedly attached to upper member 502 and heel end 514 of the wave member is adapted to be deflected. In addition, preferred lower limb prosthetic device 500 comprises second wave member 530. The preferred second wave member 530 has forward end 532 and rearward end 534. Preferably, rearward end 534 of second wave member 530 is fixedly attached adjacent to distal end 524 of third member 520 and forward end 532 of the second wave member is adapted to contact wave member 510 and upper member 502. The preferred lower limb prosthetic device 500 still further comprises mounting device 540.

Figure 31:
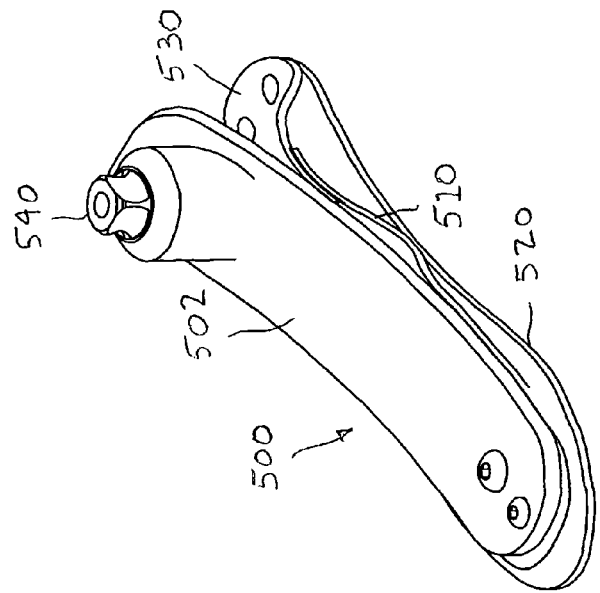
FIG. 31 is a perspective view of the preferred lower limb prosthetic device illustrated in FIG. 30.

Referring now to FIG. 31, a perspective view of the preferred lower limb prosthetic device 500 is illustrated. As shown in FIG. 31, preferred lower limb prosthetic device 500 comprises upper member 502, wave member 510, third member 520, second wave member 530 and mounting device 540.

Figure 32:
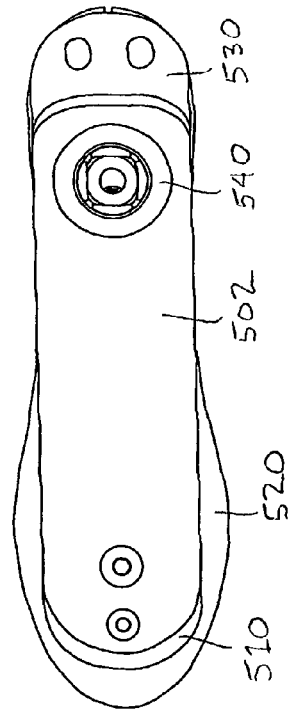
FIG. 32 is a top view of the preferred lower limb prosthetic device illustrated in FIGS. 30-31.

Referring now to FIG. 32, a top view of the preferred lower limb prosthetic device 500 is illustrated. As shown in FIG. 32, preferred lower limb prosthetic device 500 comprises upper member 502, wave member 510, third member 520, second wave member 530 and mounting device 540. While FIGS. 30-32 illustrate the preferred configuration and arrangement of lower limb prosthetic device 550, it is contemplated within the scope of the invention that the lower limb prosthetic device may be of any suitable configuration and arrangement.

In operation, several advantages of the preferred embodiments of the lower limb prosthetic device are achieved. For example, the preferred embodiments of the lower limb prosthetic device are adapted to increase the deflection and dampen the impact at heel strike. The preferred lower limb prosthetic devices are also adapted to reduce the weight and size of the prosthetic device. The preferred lower limb prosthetic devices are further adapted to improve the vertical compliance and roll over characteristics of the prosthetic device.

Although this description contains many specifics, these should not be construed as limiting the scope of the invention but as merely providing illustrations of some of the presently preferred embodiments thereof, as well as the best mode contemplated by the inventors of carrying out the invention. The invention, as described herein, is susceptible to various modifications and adaptations, and the same are intended to be comprehended within the meaning and range of equivalents of the appended claims.

What is claimed is:

1. A prosthetic device, said prosthetic device comprising:
   (a) an upper leaf spring member, said upper leaf spring member having an upper end and a lower end;
   (b) a wave leaf spring member, said wave leaf spring member having a toe end and a heel end and said wave leaf spring member disposed below the upper leaf spring member;
   (c) a third leaf spring member, said third leaf spring member having a length, a first end and a second end and said third leaf spring member disposed below the wave leaf spring member;
   wherein the toe end of the wave leaf spring member is fixedly attached to the upper leaf spring member at the lower end and the third leaf spring member at the first end; and wherein the heel end of wave leaf spring member is in continuous surface contact with the third leaf spring member regardless of loaded or unloaded states of the device and slidingly deflected along the third leaf spring member; and wherein the wave leaf spring member extends along a substantial portion of the length of the third leaf spring member.

2. The prosthetic device of claim 1 wherein said device is adapted to be worn on a user's lower limb.

3. The prosthetic device of claim 1 wherein the first end of the third leaf spring member is fixedly attached adjacent to the toe end of the wave leaf spring member.

4. The prosthetic device of claim 1 wherein the third leaf spring member comprises a slot.

5. The prosthetic device of claim 1 further comprising a dampener.

6. The prosthetic device of claim 5 wherein the dampener is resilient.

7. The prosthetic device claim 5 wherein the wave leaf spring member is in continuous contact with the dampener.

8. The prosthetic device claim 5 wherein the dampener is disposed on the upper leaf spring member.

9. The prosthetic device of claim 1 wherein the wave leaf spring member comprises an arch.

10. The prosthetic device of claim 1 wherein the wave leaf spring member is resilient.

11. The prosthetic device of claim 1 wherein the wave leaf spring member has an original configuration and is adapted to be compressed and elongated when a load is applied to the device and return to the original configuration when the load is removed from the device.

12. The prosthetic device of claim 1 wherein the wave leaf spring member is adapted to deflect along a horizontal plane and a vertical plane.

13. The prosthetic device of claim 1 further comprising a mounting device.

* * * * *